United States Patent [19]

Ott

[11] 4,250,838
[45] Feb. 17, 1981

[54] METHOD FOR SYSTEMIC CONTROL OF PARASITIC INSECTS

[75] Inventor: Jerry E. Ott, Kinston, N.C.

[73] Assignee: Farnam Livestock Equipment and Insecticides, Inc., Phoenix, Ariz.

[21] Appl. No.: 57,794

[22] Filed: Jul. 16, 1979

[51] Int. Cl.³ .................... A01K 27/00; A01K 29/00
[52] U.S. Cl. .................................... 119/106; 119/156; 424/28
[58] Field of Search ............... 119/96, 106, 109, 156; 424/28

[56] References Cited

U.S. PATENT DOCUMENTS

| 3,814,061 | 6/1974 | Aries et al. | 119/106 |
| 3,852,416 | 12/1974 | Grubb et al. | 119/106 X |
| 4,091,766 | 5/1978 | Colliard | 119/106 |
| 4,145,409 | 3/1979 | Pasarela | 119/156 X |
| 4,150,109 | 4/1979 | Dick et al. | 119/106 X |
| 4,158,051 | 6/1979 | Greenberg et al. | 119/106 X |

FOREIGN PATENT DOCUMENTS

| 2715596 | 10/1978 | Fed. Rep. of Germany | 119/156 |
| 2124776 | 9/1972 | France | 424/28 |

Primary Examiner—Gene Mancene
Assistant Examiner—Robert P. Swiatek
Attorney, Agent, or Firm—Drummond and Nelson

[57] ABSTRACT

A method for systemic control of insects on animals which includes the step of continuously contacting the skin of the animal with chlorpyrifos to establish and maintain an insecticidally effective concentration of chlorpyrifos in the animal's blood stream.

1 Claim, 5 Drawing Figures

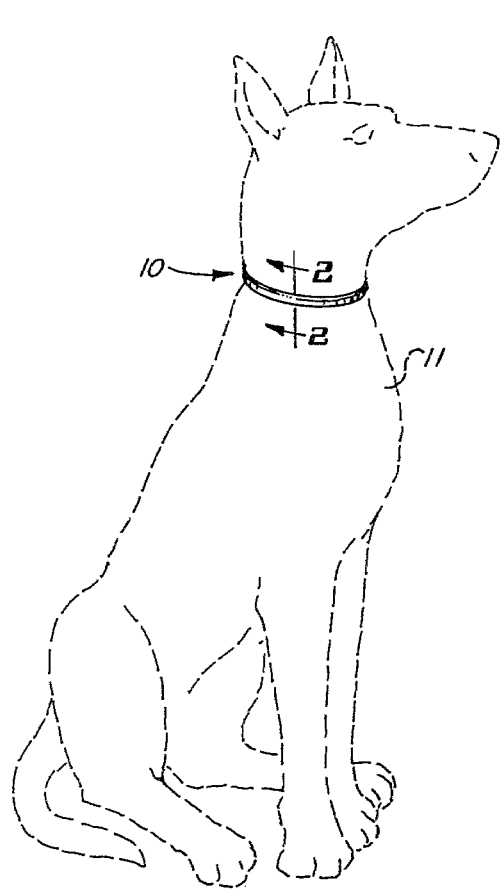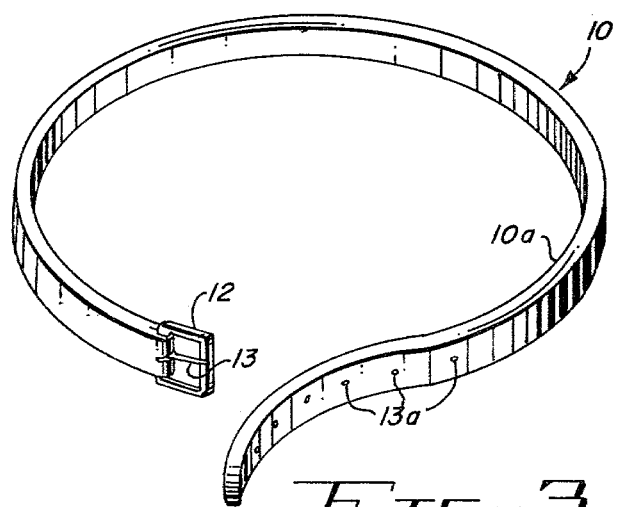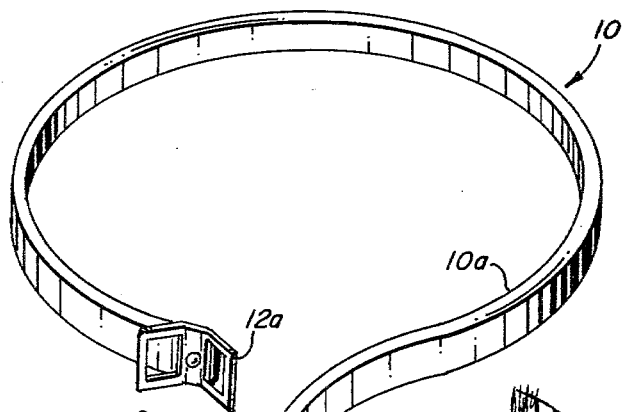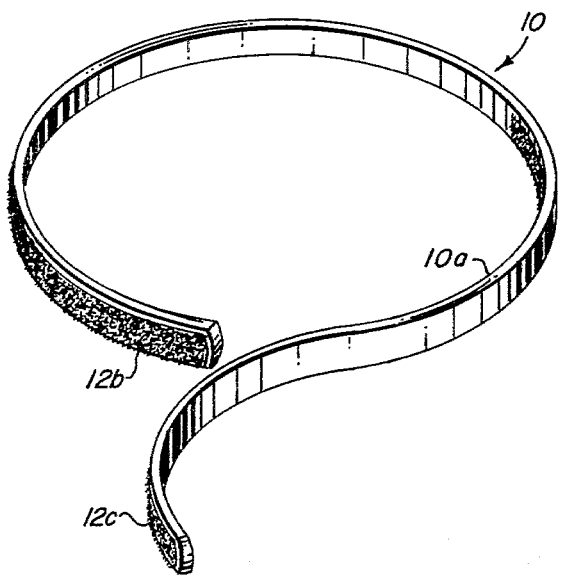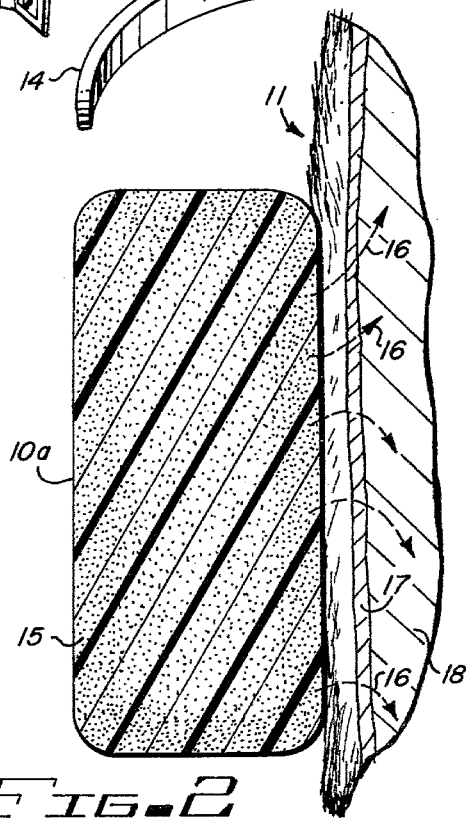

METHOD FOR SYSTEMIC CONTROL OF PARASITIC INSECTS

This invention relates to a method for systemic control of parasitic insects on animals.

In still another aspect, the invention pertains to restraining apparatus which can conveniently and continuously be employed for killing and controlling parasitic insects on animals for an extended period of time.

Harnesses for restraining animals, in particular collars which can be placed around an animal's neck, are well known in the art. Such collars are often comprised of a simple strap or band of material with a buckle on one end of the strap to secure the other end of the strap when the collar is placed around the neck of the animal. However, collars of greater complexity, where the strap consists of a number of interconnecting or layered segments of material, are also known in the art.

A wide variety of materials, including metals, leather, polyvinylchloride and cloth, have been employed in the construction of collar bands. Combinations of different materials are common. For example, plastic or metal is often layered on leather.

The collar strap is typically provided with a buckle or other fastening device which permits the fit of the collar to be adjusted. Perhaps the most prevalent means of attaching the two ends of the collar band consists of punching holes in one end of the band and then attaching to the other end of the band a belt-type buckle with a tongue that fits through the holes. A somewhat similar arrangement eliminates both the punching of holes in one end of the collar strap and the tongue in the buckle by attaching a tongue-less buckle to one end of the strap. The tongue-less buckle receives and frictionally secures the other end of the strap.

Other methods of fastening the ends of the collar band include either attaching a friction contact material like Velcro to each end of the band or providing the ends of the collar strap with attachments that will snap or screw together.

Also known in the art is the adapting of such collars for the purpose of repelling or killing parasitic insects which might otherwise inhabit the animal's body. Such so called "flea and tick collars" are commonly employed on domestic cats and dogs. The collars generally are comprised of a thermo-plastic material which is permeated with contact insecticide and then extruded to form a collar. When the collar is fastened around the animal's neck, the insecticide in the collar bleeds to the surface of the collar and is abraded from the collar surface onto the animal's fur. Parasitic insects are killed on contacting insecticide adhering to the collar or to the animal's fur.

While the prior art flea and tick collars are generally effective, they have a limited useful life of only 5 to 9 months. Also, the overall effectiveness of the prior art flea and tick collars is limited in that insects, in order to be killed, must actually come in contact with the insecticide on the collar or on the animal's surrounding fur.

Accordingly, it would be highly desirable to provide a collar for restraining animals which would kill parasitic insects that would otherwise infest the animal.

It would also be highly desirable to provide such a collar which would kill parasitic insects more effectively than prior art collars.

Further, it would be highly desirable to provide a collar which would provide continuous protection over an extended period of time greater than the period of protection of prior art flea and tick collars.

It is therefore a principal object of the present invention to provide a collar for restraining an animal which provides a means for killing parasitic insects that would otherwise inhabit the animal.

Another object of the invention is to provide such a collar which would kill parasitic insects more effectively than prior art flea and tick collars.

A further object of the invention is to provide such a collar which would provide continuous protection against parasitic insects over an extended period of time that is greater than the period of protection of prior art flea and tick collars.

These and other, further and more specific objects and advantages of the invention will be apparent to those skilled in the art from the following detailed description thereof, taken in conjunction with the drawings, in which:

FIG. 1 is a perspective view of a collar representing the preferred embodiment of the present invention fastened around the neck of a dog;

FIG. 2 is a cross-sectional view of the dog and collar of FIG. 1 taken along section line 2—2 thereof and illustrating the mode of operation of the collar;

FIG. 3 is a perspective view of the collar of FIG. 1 illustrating means for fastening the ends of the collar;

FIG. 4 is a perspective view of the collar of FIG. 1 illustrating alternative means of fastening the ends of the collar; and FIG. 5 is a perspective view of the collar of FIG. 1 illustrating yet other means for fastening the ends of the collar.

Briefly, in accordance with my invention, I provide a method for systemically controlling parasitic insects on animals. The method comprises the step of continuously contacting the skin of the animal with chlorpyrifos to establish and maintain an insecticidally effective concentration of chlorpyrifos in the animal's blood stream. According to the presently preferred embodiment of the invention, the chlorpyrifos is maintained in contact with the animal's skin by incorporating the chlorpyrifos in a polyvinylchloride collar. The collar means is at least partially constructed of a polyvinylchloride substrate containing 7.5-15% by weight of chlorpyrifos and a lubricating plasticizer. The chlorpyrifos continuously bleeds to the surface of the polyvinylchloride substrate with said plasticizer over an extended period of time to contact the skin of the animal.

In the presently preferred embodiment of the invention, the collar band consists entirely of a polyvinylchloride (PVC) substrate with 7.5-15% by weight of chlorpyrifos. The collar strap is provided with a buckle or other suitable fastener.

PVC is one of a class of generally synthetic thermoplastic polymer resins which can be "filled" with solid materials and then extruded in numerous forms. PVC, as do all vinyl plastics, contains a "plasticizer" which provides internal lubrication for and imparts flexibility to the plastic. As this gradual depletion of plasticizer takes place, the plastic becomes more brittle. Once an appropriate period of time has elapsed, and a substantial portion of the plasticizer has diffused from the plastic, the plastic may be fractured with minimal tensile force.

Chlorpyrifos is an organophosphate insecticide known to be readily absorbed through animal and human skin and is not harmful to animals in small but insecticidally-effective concentrations in the animal's blood. Chlorpyrifos (0,0-diethyl-0-3,5,6-trichloro-2-pyridylphosphorothioate) is marketed by Dow Chemical Company under the trade name "DURSBAN A".

The chlorpyrifos is mixed with PVC powder and the resultant mixture is then melted and extruded into flat strips which are cut to the desired length and provided with a buckle or other suitable fastener to form the collar.

When the collar is placed on the animal's neck, the insecticidally active chlorpyrifos, along with the plasticizer, bleeds at a controlled rate to the surface of the collar and is transferred from the collar surface to the fur and ultimately to the skin of the animal. The insecticide is absorbed through the skin of the animal and enters the animal's bloodstream. By simply leaving the collar around the animal's neck indefinitely, controlled quantities of the insecticide are maintained in contact with and absorbed through the animal's skin to maintain an insecticidally effective concentration of the insecticide in the animal's bloodstream. When a parasitic insect such as a flea, a tick or a mite punctures the animal's skin, it is contacted with the insecticide-blood composition and is killed either by contact with or by ingestion of the composition.

Present experience indicates that a collar fabricated in accordance with the presently preferred embodiment of the invention will maintain its efficiency for at least twelve months, as compared to only about 5 months for the flea and tick collars in the prior art and about 9 months for a collar effective against fleas only.

Turning now to the drawings, which depict the presently preferred embodiment of the invention for the purpose of illustrating the practice thereof and not by way of limitation of the scope of the invention, FIGS. 1-5 illustrate the presently preferred embodiment of the invention, a collar 10 with a strap 10a composed entirely of a polyvinylchloride containing 7.5-15% by weight chlorpyrifos.

FIG. 1 depicts the collar 10 fastened around the neck of a dog. The dog is represented by the dotted lines 11.

In FIG. 2, the chlorpyrifos, represented by the dots 15, permeates the polyvinylchloride strap 10a. As shown by the dotted lines 16, over an extended period of time the chlorpyrifos 15 gradually bleeds to the surface of the polyvinylchloride strap 10a, is abraded onto the fur of the dog 11 and then is absorbed through the skin 17 into the body 18 of the dog 11.

As illustrated in FIG. 3, the strap 10a of the collar 10 may be provided with a belt-type buckle 12 having a tongue 13. Apertures 13a in the strap 10a receive the tongue 13 when the collar 10 is attached about the neck of the dog 11.

In FIG. 4, the strap 10a of the collar 10 is provided with a buckle 12a which receives and frictionally secures the free end 14 of the collar strap 10a.

Another method of connecting the ends of the collar strap 10 is disclosed in FIG. 5, which depicts the strap 10a provided with negative Velcro 12c and positive Velcro 12b so that the ends of the strap 10a may simply be pressed together to fasten the collar 10 around the neck of the dog 11.

Having described my invention in such terms as to enable those skilled in the art to understand and practice it, and having identified the presently preferred embodiment thereof, I claim:

1. In a method for control of parasitic insects on animals including the step of:
   placing a collar-shaped thermoplastic substrate around the animal's neck which carries an insecticidally active ingredient,
the improvement whereby such insect control is attained systemically, comprising the steps of:
   (a) forming said thermoplastic substrate from an extrusion mixture of polyvinylchloride, a plasticizer and from about 7.5 to about 15% by weight of chlorpyrifos, said extrusion mixture being free of trivalent nitrogen compounds, alkyl amines or amides;
   (b) extruding said mixture to form an animal collar;
   (c) providing fastener means for said collar; and
   (d) placing said collar around the neck of an animal and adjusting said fastener means to maintain at least the inner surface of said collar in contact with the neck hair and skin of the animal such that chlorpyrifos which bleeds to the surface of said collar in the liquid phase directly contacts said neck hair and skin and is absorbed into the animal's bloodstream and establishes and maintains an insecticidally effective concentration of chlorpyrifos in the animal's bloodstream and on said hair and skin of the animal.

* * * * *

Disclaimer and Dedication 4,250,838.—*Jerry E. Ott*, Kinston, N.C. METHOD FOR SYSTEMIC OF PARASITIC INSECTS. Patent dated Feb. 17, 1981. Disclaimer and Dedication filed Mar. 27, 1989, by the assignee, The Dow Chemical Company.

Hereby disclaims and dedicates to the Public the remaining term of said patent.
[*Official Gazette August 8, 1989*]